United States Patent [19]
Delaunois et al.

[11] 3,975,448
[45] Aug. 17, 1976

[54] HALOGENATED ARALKYL ETHERS

[75] Inventors: Yvon Delaunois, Tessenderlo; Claude Wilante, Brussels, both of Belgium

[73] Assignee: Tessenderlo Chemie S.A., Brussels, Belgium

[22] Filed: Aug. 31, 1973

[21] Appl. No.: 393,332

[30] Foreign Application Priority Data
Sept. 8, 1972 France .............................. 72.31837

[52] U.S. Cl. ............................ 260/611 A; 252/54; 252/77; 252/65; 252/364
[51] Int. Cl.² ........................................ C07C 43/28
[58] Field of Search ............................... 260/611 A

[56] References Cited
UNITED STATES PATENTS

| | | | |
|---|---|---|---|
| 2,409,274 | 10/1946 | Hanford et al. | 260/611 A X |
| 2,564,214 | 8/1951 | Ross et al. | 260/611 A |
| 2,702,825 | 2/1955 | Ross et al. | 260/611 A |
| 2,831,033 | 4/1958 | O'Rear | 260/611 A X |
| 3,303,221 | 2/1967 | Gilbert | 260/611 A |
| 3,661,967 | 5/1972 | Anderson et al. | 260/611 A X |

*Primary Examiner*—Bernard Helfin
*Attorney, Agent, or Firm*—Millen, Raptes & White

[57] ABSTRACT

The invention relates to novel halogenated alkylaryl ethers having at least one fluoroalkyl grouping, which have very good thermal stability and chemical resistance, and to a process for producing the ethers.

5 Claims, No Drawings

HALOGENATED ARALKYL ETHERS

BACKGROUND OF THE INVENTION

This invention relates to novel halogenated alkylaryl thermostable ethers and a process for the preparation thereof.

BRIEF DESCRIPTION OF THE INVENTION

The novel ethers of this invention have the general formula:

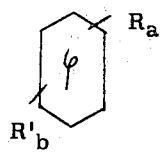
I wherein R is an aliphatic saturated radical having the formula $CH_2$—$OC_nX_{2n+1}$ and is linear or branched with one tertiary carbon atom located $\alpha$- to the oxygen atom and substituted by 2 methyl groups, $n$ is equal or greater than 3 when R is linear, or equal or greater than 4 when R is branched, X is F or H, the substituents X being only H on the carbon atom located $\alpha$ to the oxygen atom but at least one of the other substituents X being F, and wherein $a$ is 1 or 2; R' is F, Cl or Z, Z being $CH_3$, $CF_3$ or $CF_2Cl$, the substituents R' being identical or different, but only one substituent R' being Z, and $b$ is 0 or an integer from 0 to 6-$a$.

In the formula as defined above, when $a$ is equal to 2, the two radicals R can be respectively in ortho, meta or para positon on the phenyl radical, the optional substituents R' being in any other position. According as $a$ is equal to 1 or 2, monoethers or diethers are prepared.

When the products of the present invention are subjected to high temperatures, they have a very good thermal stability and chemical resistance. Due to their physico-chemical properties, i.e., low melting point, high boiling points, and high viscosities, the compounds can be used in lubrication, heat transmission, electrical insulation, hydraulic fluids, or special solvents according to their particular physical form, i.e., solid or liquid at atmospheric pressure and room temperatures.

DETAILED DESCRIPTION OF THE INVENTION

The novel ethers of the invention can also be defined by the following general formula:

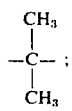
$(CH_2-O-R''-C_mX_{2m+1})_a$
II wherein R'' is —$CH_2$— or

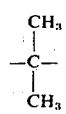
$$\begin{array}{c} CH_3 \\ | \\ -C- \\ | \\ CH_3 \end{array}$$

and $C_mX_{2m+1}$ is linear fluoroalkyl group in which X is F or H, at least one X being F; $m$ is at least 2 when R'' is —$CH_2$ and at least 1 when R'' is $$\begin{array}{c} CH_3 \\ | \\ -C- \\ | \\ CH_3 \end{array}$$

$a$ is 1 or 2; R''' is F, Cl or only one of the groups consisting of $CH_3$, $CF_3$, and $CF_2Cl$; and $b$ is 0–(6-$a$). The substituents R''' can be the same or different, however, only one of the groups $CH_3$, $CF_3$ and $CF_2Cl$ can be a substituent alone or with F and/or Cl. Preferably, $m$ is 2–6 when R'' is —$CH_2$—, and $m$ is 1–6 when R'' is

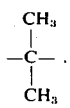
$$\begin{array}{c} CH_3 \\ | \\ -C- \\ | \\ CH_3 \end{array}$$

In the above defined general formula, when $a$ is equal to 2, the substituents —$CH_2$—O—R''—$C_mX_{2m+1}$, can be in the ortho, meta or para positions with respect to each other on the phenyl group, and the substituents R''' can be in any of the remaining positions. Thus, when $a$ is 1 or 2, monoethers or diethers are prepared.

The compounds according to the present invention are obtained by reaction of a benzyl halide(chloride, fluoride or bromide), its methyl or methyl halogenated derivatives, or one of the halogenated derivatives thereof with a halogenated aliphatic alcohol. The starting halides have the formula:

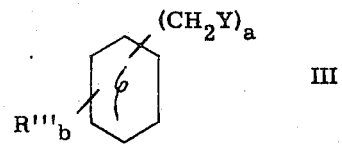
III wherein Y is F, Cl or Br, and R''', $a$ and $b$ have the same significance as defined above in Formula II.

Suitable halides particularly suitable as represented by Formula III are: benzyl chloride, bromide or fluoride; benzyl chlorides, fluorides, bromides mono-substituted in ortho, meta or para position by chlorine or fluorine; di-, tri-, tetra- or penta- substituted benzyl chlorides, fluorides or bromides substituted by chlorine and/or fluorine; tri-fluoromethyl benzyl chlorides, fluorides, bromides; methyl benzyl chlorides, fluorides or bromides; monochloro-difluoro methyl benzyl chlorides, fluorides or bromides; and xylene dichlorides, dibromides, difluorides optionally mono, di-, tri-, or tetra- substituted by chlorine and/or fluorine.

Generally the reaction can be achieved by using a chloride, a bromide or a fluoride, but for economical reasons, the chloride is preferably used as a starting material. Moreover, in the most cases, fluorides give yields lower than the chlorides.

The halogenated saturated aliphatic alcohols suitable for the present invention are either linear primary alcohols having the formula:

$C_{n-1}X_{2(n-1)+1}CH_2OH$   IV wherein X is F or H and at least one X being F, $n$ is an integer equal or greater than 3, or the corresponding tertiary alcohols of the formula:

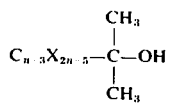

V wherein X is defined above and $n$ is equal or greater than 4 and wherein $C_{n-3} X_{2n-5}$ is linear.

In the practice of the invention, the alcohols preferably used are the alcohols either partly or entirely substituted by fluorine on the carbon atoms which do not carry the alcohol function. Among these alcohols can be cited fluorinated primary alcohols of Formula IV such as 1-propanol, 1-butanol, 1-pentanol, 1-hexanol, 1-heptanol and fluorinated tertiary alcohols of Formula V such as tert-butyl alcohol, tert-amyl alcohol, and the like.

For the practice of the invention an alkaline alcoholate is prepared according to any of the known techniques, generally sodium or potassium alcoholate of the used halogenated alcohol. For example, the halogenated alcohol can be reacted with an alkaline metal such as sodium metal in anhydrous medium or with an alkaline hydroxide such as potassium hydroxide. Then the alkaline alcoholate is reacted with the starting halide.

The reaction is achieved in the presence of a solvent inert towards the reactants such as for example, dimethyl sulfoxide, tetrahydrofuran, N, N dimethylformamide, diglyme (diethylene glycol dimethyl ether), N-methylpyrrolidine, methyl cyanide. Generally the reaction is achieved at atmospheric pressure and by heating and refluxing the reaction mixture.

The ethers, according to the present invention, can be prepared by using stoichiometric quantities of the halide and of the halogenated alcohol but preferably by using an excess of the alcohol. For example, when the reaction is carried out in the presence of metallic sodium with tetrahydrofuran an solvent, an amount of halogenated alcohol comprises within the range from 100 to 150 percent by weight, and preferably from 110 to 130 percent by weight of the molar theoretical quantity, is used. Under these conditions the reaction is relatively slow and its duration is from 2 to 20 hours to obtain a yield at least equal to 90 percent based on the used benzyl halide. When the reaction is achieved by using anhydrous alkaline hydroxide and an aprotic dipolar solvent such as dimethyl sulfoxide (DMSO), a larger excess of alcohol is generally used, this excess amounting up to 200 percent by weight of the molar theoretical quantity and being preferably comprised between 150 and 160 percent by weight. In this case, the reaction is faster and yields equal or superior to 90 percent by weight based on the used benzyl halide can be obtained in 30 to 90 minutes.

According to a preferred embodiment of the process of the invention, the reaction is achieved in a single step by introducing into the solvent the halogenated alcohol, the metal or the metallic hydroxide and the starting halide optionally dissolved in a fraction of the solvent and by heating the reaction mixture as said hereinbefore. When the reaction is completed, the reaction mixture is then treated with water to obtain on the one hand an organic phase containing the ether and the unreacted products and on the other hand an aqueous phase containing the alkaline halide formed during the reaction. These two phases are separated according to known techniques and the orginic phase is distilled off under vacuum in order to obtain the aralkyl ether. According to the used method and solvents and the nature of starting reactants, aralkyl ether yields can vary from 60 to 90 percent by weight or more based on the used benzyl halide.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

In a reaction vessel provided with a magnetic stirrer, a condenser and a dropping funnel, 1.08 mole of metallic sodium (25 g) and 1 mole of pentafluoropropanol-1 (150 g) were introduced and dissolved in 200 ml of tetrahydrofuran previously dried with sodium, thereafter 0.8 mole (100 g) of benzyl chloride in solution in tetrahydrofuran was added, and the reaction mixture was refluxed for 20 hours.

Water was then added to the reaction mixture, the sodium chloride in suspension in the aqueous phase was filtered and the organic phase was separated from the aqueous phase by extraction with ethyl ether. After decantation and washing with water, the organic phase was dried with calcium chloride and the ethyl ether was evaporated. The obtained product was distilled under vacuum.

175 g of 1,2-pentafluoropropylbenzylether were obtained, which corresponds to a yield equal to 93 percent by weight based on the amount of benzyl halide used. This ether was a liquid having the formula:

and having the following properties:
 Boiling point (B.P.): 180° C
 Melting point (M.P.): −50° C
 $n_D^{20}$: 1,4205

In a similar experiment different ethers were obtained by using pentafluoropropanol-1 and various aralkyl halides. Table 1 gives the results obtained.

EXAMPLE 2

The Example 1 was repeated by using tetrafluoropropanol-1 of formula $CHF_2CF_2CH_2OH$, and two different halides. The products obtained are shown in Table 2.

EXAMPLE 3

In a reactor vessel equipped as described in Example 1, 1.08 mole of metallic sodium (26 g) and 0.94 mole of pentafluoropropanol-1 (140 g) were dissolved into 200 ml of tetrahydrofuran previously dried with sodium, and 100 g (0.319 mole) of $\alpha, \alpha'$ 2,4,5,6-hexachloro-m-xylene in solution in tetrahydrofuran were introduced. The reaction mixture was refluxed for 20 hours.

After reaction, water was added and sodium chloride in suspension in the aqueous phase was separated from the organic phase by extraction with ethyl ether. After decantation and washing with water, the product was dried with calcium chloride and the ethyl ether was evaporated.

After distillation under vacuum, there were obtained 165 g of an oily product having the following characteristics:

| | | | |
|---|---|---|---|
| B.P. (760 mm Hg) | : 316°C | Viscosity at 20°C | : 673 cps |
| M.P. | : −40°C | Viscosity at 37.8°C | : 143.4 cps |
| $n_D^{20}$ | : 1.445 | Viscosity at 71°C | : 22.37 cps |
| $d^{20}$ | : 1.6460 | Viscosity at 99°C | : 8.41 cps |

In a similar manner, a diether was obtained by starting with m-xylene chloride and pentafluoropropanol-1. The diether was α,α-dipenta-1′,2′-fluoropropyl-m-exlene diether, which was a liquid and had the following properties:

TABLE 1

| Starting halide | Obtained ether | Physical constants of the obtained ether | N.M.R. spectrum of the obtained ether |
|---|---|---|---|
| p-ClC$_6$H$_4$CH$_2$Cl<br>p-chlorobenzyl chloride | p-ClC$_6$H$_4$CH$_2$OCH$_2$CF$_2$CF$_3$<br>1′2′-pentafluoropropyl-<br>p-chlorobenzyl ether<br>oil | B.P.: 207°C M.P.: −58°C<br>$n_D^{20}$: 1.4371<br>$d^{20}$: 1.3489<br>Viscosity at 20°C:<br>3.24. centipoises (cps) | δ $\underline{CH_2}$—O—CH$_2$ = 4.3 singlet<br>δ $\underline{CH_2}$—CF$_2$—CF$_3$ = 3.5 triplet |
| 3,4-Cl$_2$C$_6$H$_3$CH$_2$Cl<br>3,4-dichlorobenzyl<br>chloride | 3,4-Cl$_2$C$_6$H$_3$CH$_2$OCH$_2$CF$_2$CF$_3$<br>1′,2′-pentafluoropropyl-<br>3,4-dichlorobenzyl ether<br>oil | B.P.: 245°C M.P.: −101°C<br>$n_D^{20}$: 1.4591<br>$d^{20}$: 1.4634<br>Viscosity at 20°C:<br>6.14 cps | δ $\underline{CH_2}$—OCH$_2$ = 4.2 singlet<br>δ $\underline{CH_2}$—CF$_2$—CF$_3$ = 3.5 triplet |
| 2,6-Cl$_2$C$_6$H$_3$CH$_2$Cl<br>2,6-dichlorobenzyl<br>chloride | 2,6-Cl$_2$C$_6$H$_3$CH$_2$OCH$_2$CF$_2$CF$_3$<br>1′,2′-pentafluoropropyl-<br>2,6-dichlorobenzyl ether<br>oil | B.P.: 232°C M.P.: −30°C<br>$n_D^{20}$: 1.4617<br>$d^{20}$: 1.461<br>Viscosity at 20°C:<br>7.746 cps | δ $\underline{CH_2}$—O—CH$_2$ = 4.5 singlet<br>δ $\underline{CH_2}$—CF$_2$—CF$_3$ = 3.6 triplet |
| 2,4-Cl$_2$C$_6$H$_3$CH$_2$Cl<br>2,4 dichlorobenzyl<br>chloride | 2,4-Cl$_2$C$_6$H$_3$CH$_2$OCH$_2$CF$_2$CF$_3$<br>1′,2′-pentafluoropropyl-<br>2,4-dichlorobenzyl ether<br>liquid | B.P.: 232°C<br>M.P.: −93°C<br>$n_D^{20}$: 1.4608 | $\underline{CH_2}$—O—CH$_2$ = 4.4 singlet<br>$\underline{CH_2}$—CF$_2$—CF$_3$ = 3.7 triplet |
| 2,4,6-Cl$_3$C$_6$H$_2$CH$_2$Cl<br>2,4,6-trichlorobenzyl<br>chloride | 2,4 6-Cl$_3$C$_6$H$_2$OCH$_2$CF$_2$CF$_3$<br>1′,2′-pentafluoropropyl-<br>2,4,6-trichlorobenzyl<br>ether<br>oil | B.P.: 248°C<br>M.P.: −70°C<br>$n_D^{20}$: 1.4880<br>$d^{20}$: 1.5265<br>Viscosity at 20°C<br>9.34 cps | $\underline{CH_2}$—O—CH$_2$ = 4.9 singlet<br>$\underline{CH_2}$—CF$_2$—CF$_3$ = 3.8 triplet |
| C$_6$F$_5$CH$_2$Br<br>Pentafluorobenzyl<br>bromide | C$_6$F$_5$CH$_2$OCH$_2$CF$_2$CF$_3$<br>1′,2′-pentafluoropropyl-<br>pentafluorobenzyl ether | B.P.: 229°C<br>M.P.: −40°C<br>$n_D^{20}$: 1.375 | |

TABLE 2

| Starting halide | Obtained ether | Physical constants of the obtained ether |
|---|---|---|
| P-ClC$_6$H$_4$CH$_2$Cl<br>p-chlorobenzyl<br>chloride | p-ClC$_6$H$_4$CH$_2$OCH$_2$CF$_2$CF$_2$H<br>1′,2′-tetrafluoropropyl-<br>p-chloro benzyl ether | B.P.: 234°C<br>M.P.: −27°C<br>$n_D^{20}$: 1.4605 |
| 2,4-Cl$_2$C$_6$H$_3$CH$_2$Cl<br>2,4-dichloro-<br>benzyl chloride | 2,4-Cl$_2$C$_6$H$_3$CH$_2$OCH$_2$CF$_2$CF$_2$H<br>1′,2′-tetrafluoropropyl-<br>2,4-dichlorobenzyl ether | B.P.: 254°C<br>M.P.: −70°C<br>$n_D^{20}$: 1.4775<br>$d^{20}$: 1.4359<br>Viscosity = 9.13 cps at 20°C |

Table 3 gives the results of the analysis of this product. These results show that this product is a mixture of several compounds. An analytical study by using vapor phase chromatography revealed the presence of two compounds. The main compound was identified by N.M.R. spectrum, as 1′,2′-dipentafluoropropyl-2,4,5,6-chloro-m-xylene diether having the formula:

B.P.: 240° C
M.P.: −85° C
$n_D^{20}$: 1.4072
$d^{20}$: 1.3953
Viscosity at 20° C : 8.25 cps.

By using tetrafluoropropanol as the alcohol, the para- and meta-xylene dichloride, other diethers were obtained. Their properties are given in Table 4.

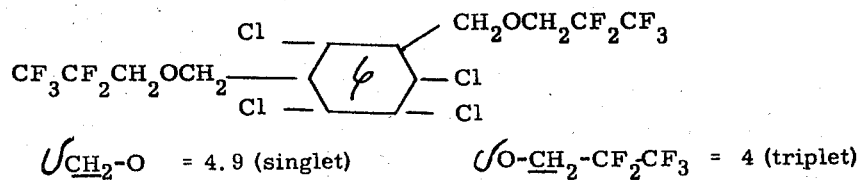

$\mathcal{U}_{\underline{CH_2}-O}$ = 4.9 (singlet)       $\mathcal{U}_{O-\underline{CH_2}-CF_2CF_3}$ = 4 (triplet)

Table 5 gives the results of the analysis of α, α-ditetrafluoro-1′,2′-propyl-p-xylene diether. It was determined that this diether was 95 % pure by using vapor phase chromatography.

TABLE 3

| Molecular weight | Calculated 540 | Found 667 |
|---|---|---|
| % C | 31.14 | 29.42 |
| % H | 1.49 | 1.41 |
| % F | 35.18 | 37.5 |
| % Cl | 26.26 | 22.4 |
| % halogen (Cl + F) | 61.14 | 59.5 |

TABLE 4

| Starting halide | Obtained ether | Physical constants | N.M.R. spectrum |
|---|---|---|---|
| p-ClCH$_2$C$_6$H$_4$CH$_2$Cl | p-C$_6$H$_4$(CH$_2$OCH$_2$CF$_2$CF$_2$H)$_2$ | B.P.: 285°C | δ CF$_2$H: 5.9 triplet of triplets |
| p-zylene dichloride | α,α′-ditetrafluoro-1′,2′-propyl-p-xylene diether oil | M.P.: −25°C<br>n$_D^{20}$: 1.423<br>d$^{20}$: 1.3712<br>Viscosity at 20°C: 22.75 cps | δ OCH$_2$CF$_2$: 3.6 triplet<br>δ CH$_2$—O : 4.4 singlet |
| m-ClCH$_2$C$_6$H$_4$CH$_2$Cl | m-C$_6$H$_4$(CH$_2$OCH$_2$CF$_2$CF$_2$H)$_2$ | B.P.: 278°C | δ CF$_2$H: 5.9 triplet of triplets |
| m-xylene dichloride | α,α′-ditetrafluoro-1′,2′-propyl-m-xylene diether oil | M.P.: −70°C<br>n$_D^{20}$: 1.4237<br>d$^{20}$ : 1.3715<br>Viscosity at 20°C: 18.64 cps | δ OCH$_2$CF$_2$: 3.6 triplet<br>δ CH$_2$—O: 4.4 singlet |

EXAMPLE 4

In a reactor vessel equipped as described in Example 1, 16.1 g (0.1 mole) of p-chlorobenxyl chloride, 2.76 g (0.12 mole of sodium), and 24 g (0.12 mole) of heptafluorobutanol-1 having the formula CF$_3$(CF$_2$)$_2$CH$_2$OH were dissolved in 60 ml of tetrahydrofuran. The reaction mixture was refluxed for 5 hours. 22.7 g of 1′,2′,3′-heptafluoropropyl-p-chlorobenzyl ether were obtained which corresponds to a yield equal to 70 percent based on the starting halide. The ether had the following formula and properties:

| B.P. | : 220°C | | |
|---|---|---|---|
| M.P. | : −27°C | δ—O—CH$_2$—CF$_2$ | = 3.6 triplet |
| n$_D^{20}$ | : 1.4225 | δ—CH$_2$—OCH$_2$ | = 4.2 singlet |

Table 6 gives the analysis results of the prepared ether.

By using potassium hydroxide instead of metallic sodium and by performing the reaction with dimethylsulfoxide as the solvent, the reaction yield was equal to 45 percent based on the starting halide.

Table 7 gives the properties of different ethers prepared by using heptafluorobutanol-1 and different aralkyl halides, the reaction being effected under the same conditions as hereabove.

The vapor phase chromatography analysis was carried out on the product obtained from m-xylene dichloride. This product contained 80 percent by weight of 1′,2′,3′-butyl-m-xylene diether.

Table 8 gives the results of the chemical analysis of this product.

TABLE 5

| Molecular weight | Calculated 366.25 | Found 366 |
|---|---|---|
| % C | 45.91 | 45.81 |
| % H | 3.85 | 4.28 |
| % F | 41.5 | 40.53 |

TABLE 6

| Molecular weight | Calculated 324.63 | Found 324 |
|---|---|---|
| % C | 40.70 | 37.69 |
| % H | 2.48 | 2.79 |
| % F | 40.97 | 39.87 |
| % Cl | 10.92 | 11.47 |
| % total halogen (Cl + F) | 51.89 | 51.34 |

TABLE 7

| Starting halide | Obtained ether | Physical constants of the obtained ether | N.M.R. spectrum |
|---|---|---|---|
| 2,4-Cl$_2$C$_6$H$_3$CH$_2$Cl<br>2,4-dichlorobenzyl chloride | 2,4-Cl$_2$C$_6$H$_3$CH$_2$OCH$_2$CF$_2$CF$_2$CF$_3$<br>1′,2′,3′,-heptafluorobutyl-2–4,-dichlorobenzyl ether | B.P. : 231°C<br>M.P. : −42°C<br>n$_D^{20}$ : 1.4355<br>d$^{20}$ : 1.5021<br>Viscosity at 20°C:7.15 cps | δ—O—CH$_2$—CF$_2$=3.7 triplet<br>δ—CH$_2$—O—CH$_2$=4.4 singlet |
| p-ClCH$_2$C$_6$H$_4$CH$_2$Cl<br>p-xylene dichloride | p-CF$_3$CF$_2$CF$_2$CH$_2$OCH$_2$C$_6$H$_4$CH$_2$—<br>OCH$_2$CF$_2$CF$_2$CF$_3$<br>α,α′1′,2′,3′ diheptafluorobutyl-m-xylyle diether | B.P. : 258°C<br>M.P. : −13°C<br>n$_D^{20}$ : 1.3903 | δ—O—CH$_2$—CF$_2$=3.6 triplet<br>δ—CH$_2$—O—CH$_2$=4.3 singlet |
| m-ClCH$_2$C$_6$H$_4$CH$_2$Cl<br>m-xylene dichloride | m-CF$_3$CF$_2$CF$_2$CH$_2$OCH$_2$C$_6$H$_4$CH$_2$—<br>OCH$_2$CF$_2$CF$_2$CF$_3$<br>α,α′-1′,2′,3′-diheptafluorobutyl-m-xylyle diether | B.P. : 252°C<br>M.P. : −78°C<br>n$_D^{20}$ : 1.3992<br>d$^{20}$ : 1.4565<br>Viscosity at 20°C:14.62 cps | δ—O—CH$_2$—CF$_2$=3.7 triplet<br>δ CH$_2$—O—CH$_2$=4.4 singlet |
| m-ClCH$_2$C$_6$Cl$_4$CH$_2$Cl<br>α,α′-2,4,5,6-hexachloro-m-xylene | m-C$_6$Cl$_4$(CH$_2$OCH$_2$CF$_2$CF$_2$CF$_3$)$_2$<br>α,α′-1′,2′,3′-diheptafluorobutyl-tetrachlorobenzyl-m-xylene dieter | B.P. : 323°C<br>M.P. : −35°C<br>n$_D^{20}$ : 1.419<br>Viscosity at 20°C:700 cps | |

TABLE 8

| Molecular weight | Calculated | Found |
|---|---|---|
| | 502.25 | 502 |
| % C | 38.26 | 39.71 |
| % H | 2.41 | 2.68 |
| % F | 52.96 | 47.05 |

EXAMPLE 5

In a reactor vessel equipped as described in Example 1, 0.06 mole (13 g) of m-trifluoromethylbenzyl chloride, 0.1 mole (20 g) of heptafluorobutanol-1, and 0.12 mole (6.72 g) of anhydrous potassium hydroxide were dissolved in 45 g of dimethylsulfoxide.

The reaction mixture was refluxed for 90 minutes, then water was added and the mixture was heated. The organic phase was washed with water, extracted with ethyl ether and purified with active carbon.

The ethyl ether was removed and the obtained product was submitted to a fractional distillation. There were obtained 17 g of 1′,2′,3′-heptafluorobutyl-m-trifluoromethylbenzyl ether having the formula m—$CF_3C_6H_4CH_2OCH_2$ $(CF_2)_2CF_3$. The reaction yield was equal to 70 percent based on the starting halide. The ether had the following properties.

B.P.: 205° C
M.P.: —108° C
$n_D^{20}$: 1.3835

EXAMPLE 6

Bu using the mode of operation of Example 1 and octafluoropentanol-1 having the formula $H(CF_2)_4CH_2OH$, other ethers were obtained. Table 10 gives the starting halide and properties of the ethers obtained.

N.M.R. spectrum achieved on the 1′,2′,3′,4-octafluoropentyl-2,4,6-trichlororbenzyl ether confirms its structure.

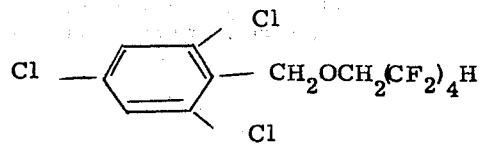

$\delta(CF_2)_4$—$\underline{H}$: 6 triplet of triplets
$\delta O$ — $\underline{CH_2}$ —$(CF_2)_4$: 4 triplet
$\delta\underline{CH_2}$—O—$CH_2$: 4.8 singlet Table 9 gives the chemical analysis of this ether.

TABLE 9

| | Calculated | Found |
|---|---|---|
| Molecular weight | 422 | 425 |
| % C | 31.9 | 33.8 |
| % H | 1.78 | 1.65 |
| % Cl | 25.96 | 25 |
| % F | 34.6 | 35.72 |
| % total halogen (Cl and F) | 60.56 | 60.72 |

EXAMPLE 7

1′H,1′H,7′H-dodecafluoroheptyl-2,4-dichlorobenzyl ether was obtained by starting from 1H,1H,7H-dodecafluoro-1-heptanol and 2,4-dichlorobenzyl dichloride.

$2,4Cl_2C_6H_3CH_2$—$OCH_2(CF_2)_5CHF_2$

B.P.: 276° C
M.P.: 45° C

EXAMPLE 8

In a reactor vessel as described in Example 1, 24 g (0.15 mole of 2-methyl-3,3,4,4-tetrafluoro-2-butanol, 15.7 g (0.12 mole) of benzyl chloride and 9.7 g (0.17 mole) of anhydrous potassium hydroxide were dissolved in 150 ml of dimethylsulfoxide. The reaction mixture was refluxed for 90 minutes. After cooling, the reaction mixture was washed with water and the organic phase was treated with ethyl ether and dried. The resulting organic phase was distilled under vacuum

TABLE 10

| Starting halide | Obtained ether | Physical constants |
|---|---|---|
| o-$ClC_6H_4CH_2Cl$<br>orthothlorobenzyl chloride | o-$ClC_6H_4CH_2OCH_2(CF_2)_4H$<br>1′,2′,3′,-octafluoro-penthyl-ortho-chlorobenzyl ether | B.P. : 243°C<br>M.P. : —75°C<br>$n_D^{20}$ : 1.4300 |
| 2,4-$Cl_2C_6H_3CH_2Cl$<br>2,4-dichlorobenzyl chloride | 2,4-$Cl_2C_6H_3CH_2OCH_2(CH_2)_4H$<br>1′,2′,3′,4;-octafluoro-pentyl 2,4 dichlorobenzyl ether | B.P. : 264°C<br>M.P. : —75°C<br>$n_D^{20}$ : 1.4505<br>$d^{20}$ : 1.5378<br>Viscosity at 20°C 10.51 cps |
| 2,4,6-$Cl_3C_6H_2CH_2Cl$<br>2,4,6-trichlorobenzyl chloride | 2,4,6$Cl_3C_6H_2CH_2OCH_2(CF_2)_4H$<br>1′,2′,3′,4′-octafluoro-penthyl 2,4,6,-trichlorobenzyl ether oil | B.P. : 284°C<br>M.P. : <—75°C<br>$n_D^{20}$ : 1.4597<br>$d^{20}$ : 1.6059<br>Viscosity at 20°C 33.52 cps |
| m-$ClCH_2C_6H_4CH_2Cl$<br>m-xylene dichloride | m $C_6H_4(CH_2OCH_2CF_2CF_2$—$CF_2CF_2H)_2$<br>α,α′-1′,2′,3′,4′,-dioctafluoro-penthyl-m-xylene diether | B.P. : 295°C<br>M.P. : <—75°C<br>$n_D^{20}$ : 1.397<br>$d^{20}$ : 1.5315<br>Viscosity at 20°C 36.55 cps |

(5mm Hg) to yield 15 g of 1,1-dimethyl-2,2,3,3-tetrafluoropropylbenzyl ether having the formula:

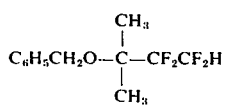

This compound was an oily liquid which had the following properties:
B.P.: 210° C
M.P.: −78° C
$n_D^{20}$: 1.4479
$d^{20}$: 1.1961
Viscosity at 20° C: 6.84 cps The yield was 54 percent by weight based on the amount of benzyl chloride used. The nuclear magnetic resonance analysis showed:
δ — $\underline{CH_2}$ — O: 4.5 p.p.m.
δ — $(CH_3)_3$ —: 1.42 p.p.m.
δ — $CF_2\underline{H}$: 6.04 p.p.m.
δ — φ: 7.33 p.p.m.

These data are consistent with and support the ether structure.

In a similar manner other ethers were obtained by starting with 2-methyl-3,3,4,4-tetrafluoro-2-butanol and different halides. Table 11 gives the starting halides used and the obtained results.

3bis (chloromethyl) benzene, 16.4 (0.29 mole) of anhydrous potassium hydroxide were dissolved in 150 ml of dimethylsulfoxide.

After reaction, 13 g of an oily product were obtained, which corresponds to a yield equal to 33 percent by weight based on the amount of halide used. The ether had the following properties:
B.P.: 305° C
M.P.: −45° C
$n_D^{20}$: 1.4392
$D^{20}$: 1.2856
γ20: 55.52 cps
N.M.R. analysis showed:
δ $\underline{CH_2}$—O: 4.5 p.p.m.
δ $(CH_3)_2$: 1.4 p.p.m.
δ $CF_2\underline{H}$: 5.46 p.p.m.
δ — φ—: 7.3 p.p.m.

The data supports the following ether structure:

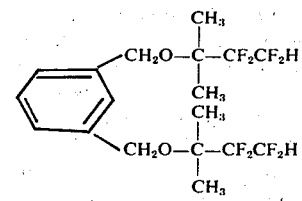

TABLE 11

| Starting halide | Obtained ether | Physical constants of the obtained ether | N.M.R. spectrum of the obtained ether | |
|---|---|---|---|---|
| p-ClC$_6$H$_4$CH$_2$Cl p-chlorobenzyl chloride | p-ClC$_6$H$_4$CH$_2$OC(CH$_3$)$_2$—CF$_2$CF$_2$H 1,1-dimethyl-2,2,3,3-tetrafluoropropyl-p-chlorobenzyl ether | B.P.:230°C M.P.:−8°C $n_D^{20}$ : 1.4649 $d^{20}$ : 1.2828 $\gamma^{20}$ : 10.88 cps | δ—CH$_2$—O δ—(CH$_3$)$_2$— δ—CH$_2$H— δ—φ— | =4.48 p.p.m. = 2.4 p.p.m. = 6 p.p.m. =7.25 p.p.m. |
| 2,4-Cl$_2$C$_6$H$_3$CH$_2$Cl 2,4-dichlorobenzyl chloride | 2,4-Cl$_2$C$_6$H$_3$CH$_2$OC(CH$_3$)$_2$CF$_2$CF$_2$H 1',1'-dimethyl-2',2',3',3'-tetrafluoropropyl-2,4-dichlorobenzyl ether | B.P.:270°C M.P.:−10°C $n_D^{20}$ : 1.4776 $d^{20}$ : 1.3683 $\delta^{20}$ : 15.97 cps | δ—CH$_2$—O δ—(CH$_3$)$_2$— δ—CF$_2$H δ—φ< | =4.6 p.p.m. =1.5 p.p.m. =6 p.p.m. = 7.29 p.p.m. |
| 3,4-Cl$_2$C$_6$H$_3$CH$_2$Cl 3,4-dichlorobenzyl chloride | 3,4Cl$_2$C$_6$H$_3$CH$_2$OC(CH$_3$)$_2$CF$_2$CF$_2$H 1',1'-dimethyl-2',2',3',3'-tetrafluoropropyl-3,4-dichlorobenzyl ether | B.P.:280°C M.P.:10°C $n_D^{20}$ : 1.4851 $d^{20}$ : 1.3743 $\delta^{20}$ : 15.99 cps | δ—CH$_2$—O δ—(CH$_3$)$_2$ δ—(CF$_2$H) δ—φ< | = 5.25 p.p.m. = 1.65 p.p.m. =7.05 p.p.m. = 8.6 p.p.m. |
| 2,6-Cl$_2$C$_6$H$_3$CH$_2$Cl 2,6-dichlorobenzyl chloride | 2,6-Cl$_2$C$_6$H$_3$CH$_2$OC(CH$_3$)$_2$CF$_2$CF$_2$H 1',1'-dimethyl-2',2',3',3'-tetrafluoropropyl-2,6-dichlorobenzyl ether | B.P.:273°C M.P.:17°C $n_D^{20}$ : 1.4798 $d^{20}$ : 1.3730 $\delta^{20}$ : 26.39 cps | δ—CH$_2$—O δ—(CH$_3$)$_2$ δ—CF$_2$H δ—φ— | = 5.25 p.p.m. = 1.5 p.p.m. = 6.75 p.p.m. =8.2 p.p.m. |
| 2,4,6-Cl$_2$C$_6$H$_2$CH$_2$Cl- 2,4,6-trichlorobenzyl chloride | 2,4,6Cl$_2$C$_6$H$_2$CH$_2$OC(CH$_3$)$_2$CF$_2$CF$_2$H 1',1'-dimethyl-2',2',3',3'-tetrafluoropropyl-2,4,6-trichlorobenzyl ether | B.P.:280°C M.P.:45°C $n_D^{20}$ : 1.5529 solid | | |

EXAMPLE 9

In a reactor vessel as described in Example 1 and the procedure therein, 40 g (0.249 mole) of 2-methyl 3,3,4,4-tetrafluoro-2-butanol, 18 g (0.104 mole) of 1, α,α'-di(1',1'-dimethyl-2',2',3',3'-tetrafluoropropyl)-m-xylene diether.

In a similar manner, the α,α'-di(1',1'-dimethyl-2',2',3',3',-tetrafluoropropyl)-p-xylene diether was obtained by using the 1,4-bis-(chloromethyl) benzene. The obtained product was a solid having the following properties:

B.P.: 300° C
M.P.: 30°–34° C
$n_D^{20}$: 1.4384
N.M.R. spectrum
δ $\underline{CH_2}$ — O: 4.5 p.p.m.
δ $(CH_3)_2$: 1.4 p.p.m.
δ $CF_2\underline{H}$: 6 p.p.m.
δ — φ: 7.25 p.p.m.

The N.M.R. spectrum of the ethers obtained according to the present invention were achieved by using a 60 M.C. apparatus and the molecular weights were determined by mass spectrography.

The chemical settings (δ) of the N.M.R. spectrum are given in parts per million (p.p.m.).

What is claimed is:

1. An ether selected from the group consisting of 1',1'-dimethyl-2',2',3',3'-tetrafluoropropyl-2,4-dichlorobenzyl ether; 1',1'-dimethyl-2',2',3',3'-tetrafluoropropyl-3,4-dichlorobenzyl ether; 1',1'-dimethyl-2',2',3',3'-tetrafluoropropyl-2,6-dichlorobenzyl ether; and α,α'-di(1',1'-dimethyl-2',2',3',3'-tetrafluoropropyl)-m-xylene diether.

2. The ether of claim 1,

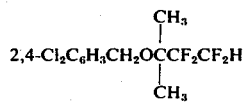

1',1'-dimethyl-2',2',3',3'-tetrafluoropropyl-2,4-dichlorobenzyl ether.

3. The ether of claim 1,

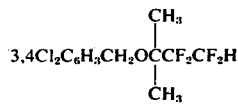

1',1'-dimethyl-2',2',3',3'-tetrafluoropropyl-3,4-dichlorobenzyl ether.

4. The ether of claim 1,

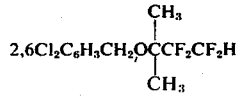

1',1'-dimethyl-2',2',3',3'-tetrafluoropropyl-2,6 dichlorobenzyl ether.

5. The ether of claim 1,

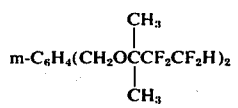

α,α'-di(1',1'-dimethyl-2',2',3',3' tetrafluoropropyl)-m-xylene diether.

* * * * *